Figure 1:
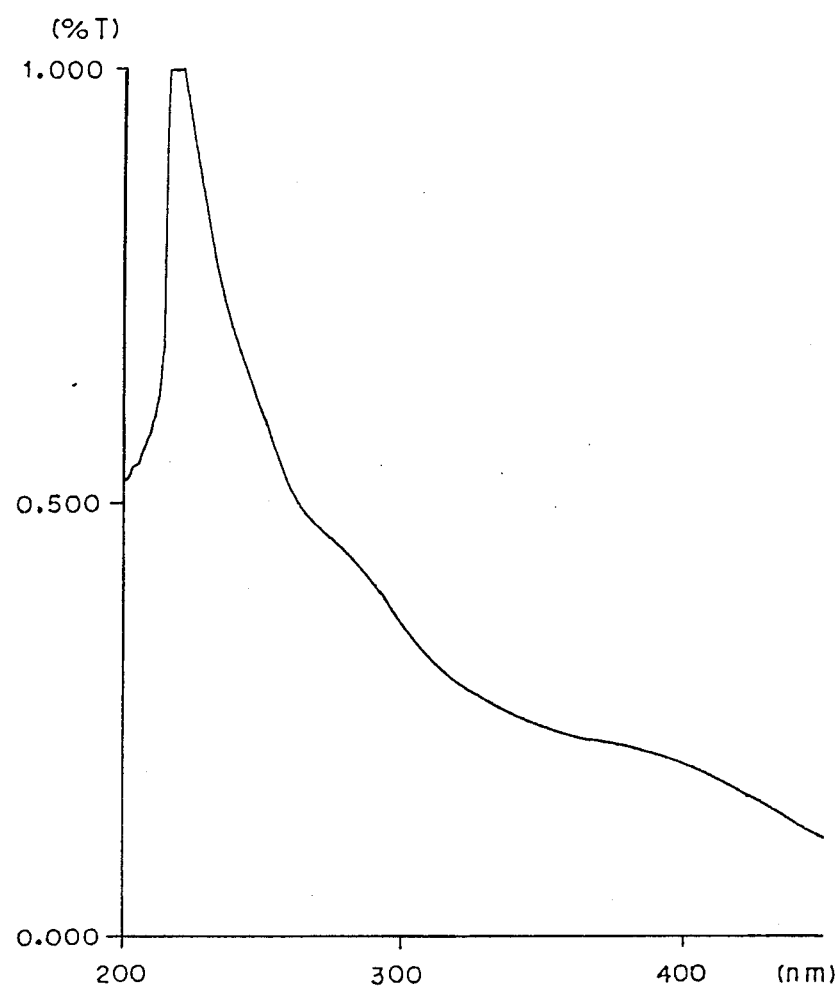

United States Patent [19]

Kojima et al.

[11] Patent Number: 4,871,540

[45] Date of Patent: Oct. 3, 1989

[54] PROCESS FOR PRODUCING A BIOLOGICALLY ACTIVE SUBSTANCE AND COMPOSITIONS CONTAINING THE SAME

[75] Inventors: Yasuhiko Kojima, 244-9, Kosugaya-cho, Totsuka-ku, Yokohama-shi, Kanagawa-ken, Japan; Sadao Tamamura, Tokyo, Japan

[73] Assignee: Yasuhiko Kojima, Japan

[21] Appl. No.: 887,168

[22] Filed: Jul. 17, 1986

[30] Foreign Application Priority Data

Jul. 17, 1985 [JP] Japan ................................ 60-157843

[51] Int. Cl.$^4$ ............................................. A61K 35/78
[52] U.S. Cl. .................................. 424/195.1; 514/885
[58] Field of Search ...................... 424/195.1; 514/885

[56] References Cited

PUBLICATIONS

Wren, R. C., Potter's Cyclopedia of Botanical Drugs and Preparations, 1950, p. 108.

Chem. Abst. 90:184731b, 1979.

*Primary Examiner*—John W. Rollins
*Attorney, Agent, or Firm*—Wolder, Gross & Yavner

[57] ABSTRACT

A biologically active substance comprising a kind of glycolipid having an elemental analysis (%) of H: 5.20–5.40, C: 42.55–44.17 and N: 3.94–4.08 and a molecular weight of about $30,000-10^6$ is obtained by extracting the tissue of a plant of maize (*Zea mays* Linne) or a variant thereof by extracting the tissue with water and recovering the desired active substance from the resultant extract. This substance is capable of inhibiting the formation of IgE antibodies and promoting the formation of IgG and IgM antibodies, and moreover exhibits various biological activities such as interferon-inducing activity, polyclonal B lymphocite activating activity, mitrogenic activity, adjuvant activity and anti-tumour activity. Thus, this substance is expected to be useful for preventing and treating, for example, aesthema, rhinitis, B-type hepatitis, AIDS and other allergic diseases and immunological insufficiency.

10 Claims, 2 Drawing Sheets

PROCESS FOR PRODUCING A BIOLOGICALLY ACTIVE SUBSTANCE AND COMPOSITIONS CONTAINING THE SAME

FIELD OF THE INVENTION

This invention relates to a process for producing a substance of plant origin, which has interferon-inducing activity, IgE-inhibiting activity and various other biological activities and an immuno-pharmacological composition containing the same.

DESCRIPTION OF THE PRIOR ART

Various interferon inducers of plant origin are known. The present inventors have disclosed that various plants belonging to *Angelica acutiloba, Perilla, Artemisia, Carthamus,* gourds, *Bupleurum falcatum* and the like are capable of producing interferon inducers. It is also known that various plants belonging to *Aurantii immaturi fructus, Bupleurum falcatum, Schizandrae fractus, Scutellaria baicalensis, Zizyphus vulgaris, Firtillaria venticillata, Magnolia cortex* and *Nandinae fructus* produce substances capable of inhibiting the formation of IgE antibodies in the body of humans and animals (herein referred to as IgE inhibitor). Also, the present inventors have disclosed that the plants belonging to *Coix lacrymaJobi* (pearl barley), *Prunus yedonensis, Quercus ramnus et Cortex, Smilax glabra, Angelica pubescens* and *Glycyrrhiza* sp. are capable of producing IgE inhibitors. Among them, *B. falcatum* is only one known plant capable of producing a substance having both interferon-inducing and IgE inhibiting activities. However, this plant has been used over many years as one of the most important herbs for the traditional Sino-Japanese medicine so that its supply is limited and expensive.

On the other hand, allergic diseases are, in general, classified into 4 (from I to IV types). For example, asthema, penicillin shock and allergic rhintis (e.g. pollinosis and hay fever) are classified into I type. The syndromes of I type are generally classified into the following 3 phases First phase: Where antigens come into the body of humans, IgE antibodies are formed by the action of B lymphocites to challenge the coming antigens. IgE antibodies adher to the surfaces of the mast cells to results in the socalled sensititation.

Second phase: Where the antigens of the same type further come into the body, the IgE antibodies adhering to the mast cells react with the newcomers so that chemical mediators such as histamine, SRS-A and the like are liberated from the mast cells.

Third phase: The liberated chemical mediators do harm to the tissues to induce the socalled allergic reaction.

Thus, in order to treat the allergic diseases of Type I with good results, the key issue is which phase is treated. For example, disodium chromoglycate (DSCG) and baicalen extracted from *Scutellaria baicalensis* (a plant of the genus *Perilla*) used for treating asthema are active upon the second phase so that allergic diseases may be inhibited temporarily. In order to inhibit, for example, asthema drastically and completely, it is necessary to prevent or inhibit the formation of IgE in the first phase. Various proposals have hitherto been made to prevent or inhbit the formation of IgE antibodies in the first phase. However, to our knowledge, none of such proposals has been used in practice with good results since they prevent or inhibit the formation of IgG and IgM antibodies which are important for resisting against various infectious diseases.

The present invention is based upon the discovery that a substance which we have isolated from various plants of maize (*Zea mays* Linne) exhibits a high activity of preventing or inhibiting the formation of IgE antibodies and promoting the formation of IgG and IgM antibodies and moreover capable of exhibiting interferon-inducing activity, mitogenic activity, adjuvant activity and various other interesting biological activities (hereinafter referred to as immuno-pharmacological activity) and that this substance may be produced simply and cheaply.

SUMMARY OF THE INVENTION

The present invention is directed to provide a process for producing a biologically active substance of plant origin, having interferon-inducing activity, IgE-inhibiting activity (as hereinbefore defined), an ability to promote the formation of IgG and IgM antibodies, mitogenic activity and various other activities as hereinafter disclosed and immuno-pharmacological compositions containing the same.

In one aspect of the present invention, we provides a process for producing an immuno-pharmacologically active substance of plant origin, which comprises extracting a water-soluble high molecular weight substance having biological activities with water from the tissue of a plant selected from maize (*Zea mays* Linne) of the family *Gramineae* and variants thereof capable of producing said biologically active substance, and recovering said active substance from the extract thereby obtained.

According to another aspect of the present invention, we provide an immuno-pharmacological composition which comprises as active ingredient the biologically active substance produced by the process of the present invention, in association with a pharmaceutically acceptable carrier or excipient.

The active substance of this invention is, when purified, stable in the form of amorphous light brownish powders having the following physico-chemical and biological characteristics

(I) Physico-chemical characteristics (1) Elementary analysis:
H 5.20–5.40 %, C: 42.55–44.17 %, N: 3.94–4.08 %
(Ash: 0.057 mg in 1.834 mg of sample)

(2) Molecular weight:
About 300,000–1,000,000 by gel filtration (3) Melting point or decomposing point:
Melting point is indefinite. Decomposed at about 220° C.

(4) Ultraviolet absorption spectrum:
As shown in FIG. 1 (0.1N NaoH)

Figure 2:
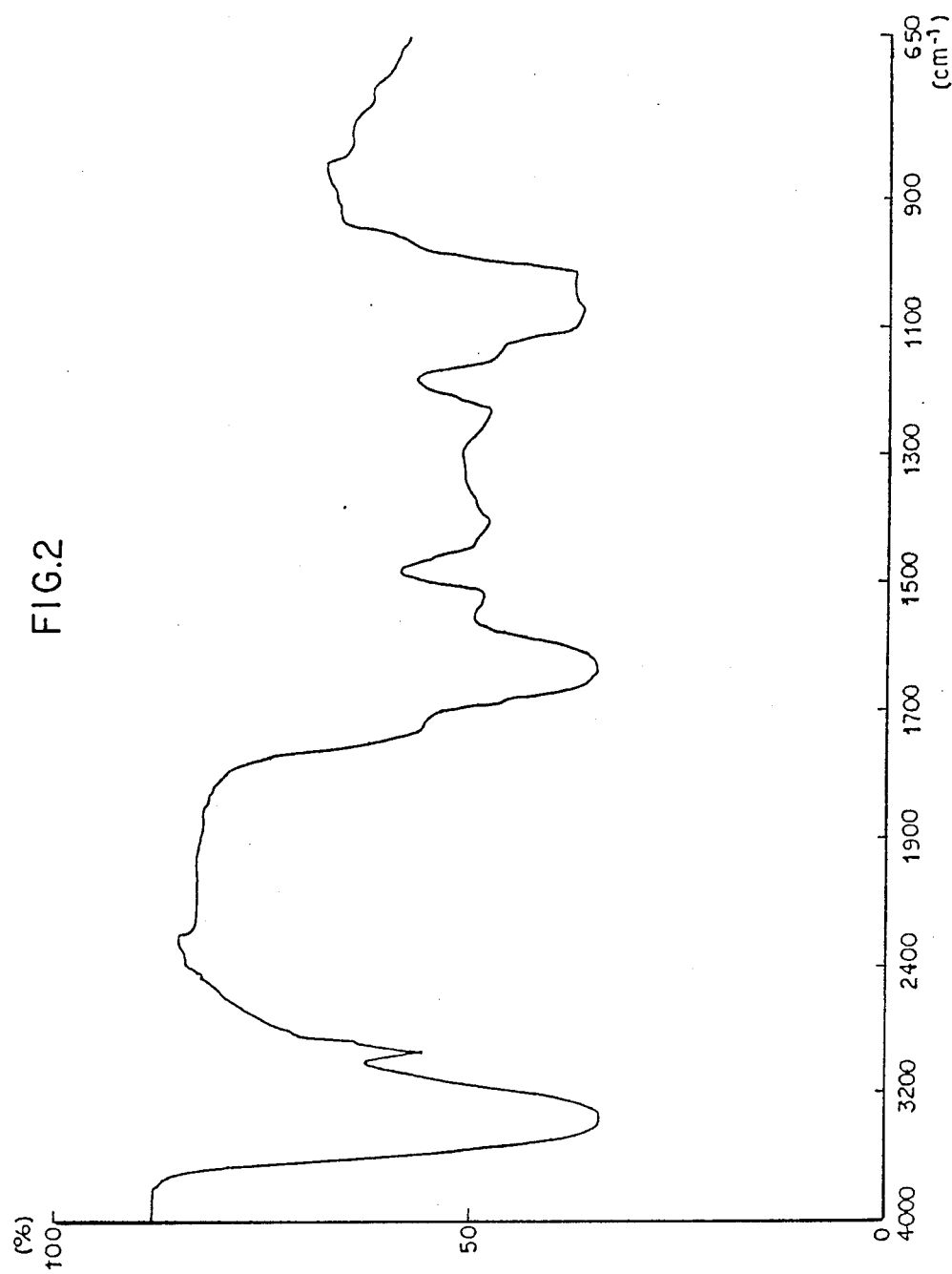

(5) Infrared absorption spectrum:
As shown in FIG. 2 (KBr method)

(6) Solubility in various solvents:
Soluble in water, readily soluble in aqueous solutions of potassium hydroxide, sodium hydroxide, ammonium hydroxide, potassium carbonate etc. and hardly soluble in methanol, ethanol, propanol, butanol, acetone, chroloform and ether.

(7) Color reaction:

Positive in ninhydrin reaction, phenol/sulfuric acid reaction and Dittmer's reaction. Negative in Morgan/Elson's reaction.

(8) Nature: acidic substance
(9) Main chemical constituents:
(A) Amino acid:

| | |
|---|---|
| aspartic acid (1.96 ± 0.02), | threonine (1.17 ± 0.02), |
| serine (1.16 ± 0.05), | glutamic acid (1.42 ± 0.01), |
| proline (0.94 ± 0.01), | glycine (2.07 ± 0.03), |
| alanine (1.71 ± 0.03), | cystine (0.12 ± 0.01), |
| valine (1.00 ± 0.03), | methionine (0.09 ± 0.02), |
| isoleucine (0.51 ± 0.01), | leucine, (1.00), |
| thyrosine (0.35 ± 0.05), | phenyalanine (0.60 ± 0.01), |
| lysine (0.55 ± 0.02) | histidine (0.18 ± 0.01), |
| arginine (0.48 ± 0.02), | ammonia (4.27 ± 0.22). |

Determined by the use of Hitachi High Performance Amino Acid Analyzer (Hitachi Limited., Tokyo) after hydrolysis with 6NHcl (110° C., 24 hr.) and expressed by the ration of the concentration on the basis of leucine (55.11 n mol=1). (B) Sugars:.(molar ratio, %) rhamnose (5.9), arabinose (3.8), xylose (4.4), mannitol (1.0), galactose (1.8), glucose (18.9), hexose in total (50.6) by phenol/sulfuric acid method, uronic acid in total(10.5 %) by metahydroxy/diphenyl method.

(10) Specific rotation:
$[\alpha]_D 25 = +30°-36°$ (33° in average, c=1 mg/ml water.

(II) Biological characteristics (1)(a) Interferon-inducing activity (rabbit):

A sample prepared by the method of Example 1 described hereinafter was used to induce interferon in the cells (in vitro) and serum (in vivo) of rabbit. The activity of the interferon induced was asayed by the methods of Experiment 1. The results shown in Tables 1 and 2 indicate the induction of interferon.

TABLE 1

| | (in vitro) | | | |
|---|---|---|---|---|
| Concentration | 10 | 1.0 | 0.1 | 0.01 (μg) |
| IFN titre | 660 | 450 | 130 | 15 |

Note:
rabbit lymphoid cells.
Administered once.

TABLE 2

| | (in vivo) | | | | |
|---|---|---|---|---|---|
| Rabbit | before | 1 | 2 | 4 | 6 (hours after) |
| 1 | <15 | 20 | 140 | 50 | 40 |
| 2 | <15 | 80 | 240 | 40 | 20 |

Note:
Hours before or after administration once (ip) at a dose of 1 mg/once.
<15... undetectable The results shown in Table 2 indicate that the interferon-inducing activity in the rabbit serum reaches its maxium about 2 hours after administration of the sample. From these tables, it has been confirmed that the present substance has interferon-inducing activity.

(b) Interferon-inducing activity (mouse)

The methods described in Experiment 1 (b) and (c) were effected by using ddY mice (female, 6 weeks after birth, each group consisting of 5 mice) to confirm the interferon-inducing activity of the present substance. The sample was administered intravenously (Table 3) or orally administered at a dose of 5 mg/kg (Table 4). The activity in the blood of the test mice was assayed in a similar manner to that described in Experiment 1 hereinafter by using mouse L cells. No activity was found by administration of the sample at a dose of 1 mg/Kg.

TABLE 3

| Induction of interferon in vivo (mouse; iv.) | | | | |
|---|---|---|---|---|
| Dose iv. mg/kg | 1 | 2 | 3 | 5 (hour*) |
| 0 | 120 | 420 | 72 | 60 |
| 4 | 36 | 108 | 24 | <15 |
| 0.4 | 42 | 30 | <15 | <15 |
| 0.04 | <15 | <15 | <15 | <15 |
| PBS (control) | <15 | <15 | | |
| Untreated | <15 | <15 | | |

Note:
*... hours after administration (once).
<15... undetectable.

TABLE 4

| Induction of interferon in vivo (mouse; oral) | | | | |
|---|---|---|---|---|
| Hours after** | 2.5 | 5 | 7.5 | 10 | 20 |
| IFN activity | <15* | <15* | <15* | 30 | <15* |

Notes:
*undetectable.
**hours after administration once (5 mg/kg).
<15... undetectable.

(2) Inhibition of the formation of IgE: (mouse abdominal)

In a similar manner to that described in Experiment 3 described hereinafter, the sample of the active substance of the invention was given to BALB/c mice (female, 6 weeks after birth, each group consisting of 5 mice). The administration was effected once at a dose of 0.5 mg/mouse. The results are shown in Table 5.

TABLE 5

| | (Inhibition of IgE formation) | | | |
|---|---|---|---|---|
| Dose, ip. | 10 | 30 | 100 | 300* |
| 0,5 mg | — | — | — | —(undetectable) |
| Physiological saline** | +++ | +++ | ++ | + |

Note: *dilution ratio of the serum.
**Untreated.

In similar manner to that hereinafter-described in Experiment 3, the sample was orally administered to BALB/C mice (each group consisting of 5 female mice, 6 weeks after birth) at a daily dose of 5 mg or 1.0 mg/mouse. The administration was continued for 3 weeks and for one week after administration of allergen. 14 days after administration of allergen, blood was collected from each mouse and treated by the method of experiment 3 to give the results shown in Table 6.

TABLE 6

| | (Inhibition of IgE formation) | | | |
|---|---|---|---|---|
| Dose/mouse | 10 | 30 | 100 | 300* |
| 5 mg/kg (×28) | ++ | + | + | — |
| 1 mg/kg (×28) | | ++ | ++ | + |
| Untreated + | +++ | +++ | ++ | + |

Note:
*dilution ratio of serum.

By abdominal administration of the active substance of this invention, the formation of IgE was significantly inhibited. By oral administration, the inhibiting effect of the active substance was relatively weak. When oral administration of the active substance was continued for 10 days after administration of allergen, no inhibition was noted.

Although not shown in these tables, intravenous administration of the active substance inhibited the formation of IgE antibodies strongly.

(3) Polyclonal B lymphocite activating activity (PBA):

In a similar manner to that described in Experiment 4 hereinafter, the active substance was given to BALB/c mice (6 weeks after birth, each group consisting of 5 female mice) to give the results shown in Table 7.

TABLE 7

| | (PBA) Anti-TNP horse red cells | | | |
|---|---|---|---|---|
| Dose($\mu$g) | PFC/culture* | T/C | PFC/spleen cells** | T/C |
| 10 | 790 ± 232 | 3.8 | 865 | 5.4 |
| 100 | 2459 ± 347 | 11.9 | 4996 | 31.2 |
| Control | 207 ± 72 | | 160 | |

Notes:
T/C = PFC (plaque forming cells) of the test group/PFC of the control group.
*... In vivo.
**... In vitro.

It was found that the active substance of this invention stimulates B cells of mouse non-specifically and enhance the formation of antibody-forming cells both in vitro and in vivo.

(4) Mitogenic activity

In a similar manner to that described in Experiment 5 hereinafter, mitogenic activity of the present active substance was assayed by the use of C3H/HeJ mice which are unreactive with the lipopolysaccharide (LPS) in bacterial endotoxin and nu/nu mice having no B lymphocyte cell. The concentration of the sample was 1, 3, 10, 30 or 100 $\mu$ g per 0.2 ml. The results are shown in Tables 8 and 9.

TABLE 8

| Mitogenic activity (spleen cells of C3/HeJ mouse) Incorporation of $^3$H—thymidine | | | |
|---|---|---|---|
| | Dose($\mu$g/well) | Incorporation (cpm) | SI |
| Control | — | 5,399 ± 294 | — |
| LPS | 10 | 7,603 ± 3,225 | 1.4 |
| Sample | 1 | 39,111 ± 3,292 | 7.2 |
| | 3 | 43,871 ± 2,667 | 8.1 |
| | 10 | 78,754 ± 7,237 | 14.6 |
| | 30 | 121,293 ± 2,220 | 22.5 |
| | 100 | 119,239 ± 14,045 | 22.1 |

Note:
LPS..LPS of endotoxin derived from Escherichia coli (commercial product of Difco., U.S.A. E. coli B:5) activity is negative. The present active substance was reactive with C3H/HeJ mouse and showed a mitogenic activity.

LPS is unreactive with C3H/HeJ mouse and its mitogenic activity is negative. The present active substance was reactive with C3/HeJ mouse and showed a mitogenic activity.

TABLE 9

| Mitogenic activity (spleen cells of nu/nu mouse***) | | | |
|---|---|---|---|
| | Dose* | Incorporation**(cpm) | SI |
| Control | — | 3,341 ± 421 | |
| LPS | 10 | 152,411 ± 3,242 | 45.6 |
| Sample | 1 | 39,141 ± 740 | 11.7 |
| | 3 | 59,744 ± 706 | 17.6 |
| | 10 | 85,391 ± 4,890 | 25.6 |
| | 30 | 151,445 ± 16,475 | 45.3 |
| | 100 | 132,424 ± 12,764 | 39.6 |

Notes:
*ug/well.
**incorporation of $^3$H—thymidine.
***6 weeks after birth, each group consisting of 5 mice It was found that the mitogenic activity was induced in nu/nu mouse having no T cell by the action of the present active substance, presumably upon B cells.

(5) Assay of adjuvant activity

Adjuvant activity of the present active substance was assayed in vivo by the method of hereinafter described Experiment 6. As test animals, BALB/s mice (8 weeks after birth, female, each group consisting of 5 mice). Sheep red cells (about $10^7$ cells) and 10 or 100 ug of the sample were simultaneously injected into the abdomen of each mouse. 4 days after this, the number of PFC (plaque forming cells) in the spleen cells of the mouse was counted. The results are shown in Table 10.

TABLE 10

| | (adjuvant activity) PFC/spleen cells* | | | |
|---|---|---|---|---|
| Antigen | Anti-SRD | T/C | Anti-HRC | T/C |
| SRC alone | 11.164 (1.74) | | 64 (2.05) | |
| Sample 10 $\mu$g | 81.617 (1.27) | 7.3 | 394 (1.85) | 6.2 |
| 100 $\mu$g | 167.040 (1.73) | 15.0 | 515 (1.78) | 8.0 |

Notes:
Anti-SRC... Anti-sheep red cell,
Anti-HRC... Anti-horse red cell,
SRC... Sheep red cell
PFC...geometric mean value from 5 mice of test group.

(6) Macrophage activatiing activity:

In a similar manner to that described in Experiment 7, macrophage activating activity was assayed by the use of macrophages obtained from BALB/c mice, EL-4 leukemia cells and the active substance prepared by the method of Example 1 (10 or 100 $\mu$g). The test was carried out twice to obtain the results shown in Table 11, from which it is apparent that the active substance of the invention has the macrophage activating activity.

TABLE 11

| | (macrophage activating activity) | |
|---|---|---|
| Antigen | $^3$H—thymidine | % cystostasis |
| Test 1 | | |
| (A) macrophage | 2,841 ± 1,015 | |
| (B) EL-4 | 72,103 ± 2,448 | |
| (A) plus (B) | 59,636 ± 7,175 | 21.2 |
| Sample (10 $\mu$g) | 5,231 ± 783 | 96.7 |
| (30 $\mu$g) | 861 ± 250 | 102.7 |
| (100 $\mu$g) | 1,782 ± 419 | 101.5 |
| Test 2 | | |
| (A) macrophage | 2,777 ± 1,041 | |
| (B) EL-4 | 57,964 ± 2,545 | |
| (A) plus (B) | 51,829 ± 8,767 | 15.4 |
| Sample (10 $\mu$g) | 39,616 ± 4,101 | 36.4 |
| (30 $\mu$g) | 33,912 ± 3,654 | 46.3 |
| (100 $\mu$g) | 20,056 ± 3,206 | 70.2 |

Note:
dose ($\mu$g/well).

(7) Anti-IMC ascites tumor activity:

Assayed in a similar manner to that described hereinafter in Experiment 8 to obtain the results shown in Table 12.

TABLE 12

| | (anti-ascites tumor activity) | | | | | | | | |
|---|---|---|---|---|---|---|---|---|---|
| Material | Survival days | | | | | | | MSD | ILS |
| Saline alone | 15 | 15 | 15 | 15 | 17 | 17 | 19 | 15 | 0 |
| Sample 25* | 28 | 31 | 34 | 37 | 39 | C | C | 37 | 147 |
| 5* | 13 | 23 | 38 | C | C | C | C | >60 | >300 |

TABLE 12-continued

| Material | (anti-ascites tumor activity) Survival days | MSD | ILS |
|---|---|---|---|
| 1* | 13 13 41 43 C C C 43 | | 187 |

Notes:
Dose: injection(ip.) mg/kg/day (once daily),
Saline: physiologycal saline solution
Sample: dissolved in physiological saline solution.
MSD: median survival days.
ILS. . . increased life spun (%) (%), C: cured (8) Anti-Ehrlich tumor activity:

Assayed in a similar manner to that described in Expriment 9 hereinafter. The results are shown in Table 3. Also note Table 12.

TABLE 13

| Dose (mg/kg/day) | Survival days | MSD | ILS |
|---|---|---|---|
| Saline alone* | 21 21 22 23 28 29 30 31 31 | 25.5 | 0 |
| *Sample 5 mg** | 19 19 21 23 42 52 C. C. C. C. | 47 | 84 |
| *Sample 1 mg** | 19 20 23 28 38 42 52 58 C. | 39.5 | 55 |

(9) Antiviral activity:

BALB/c mice and Herpes simplex virus (Miyama strain) were used to confirm the elongation of life spun by the action of the present substance, and also ddY mice and Vaccinia virus were used to found inhiting activity of the present substance against the erythema at the tail of the animals. The used animals were 6–8 weeks after birth and each group consisted of 5 mice.

(10) Acute toxicity:

The active substance was abdominally or orally administered to ddY mice (6 weeks after birth, male and female, body weight 21 ±1 g, each group consisting of 10 mice). $LD_{50}$ was 550 mg/kg (ip.) or >4 g/kg (oral). No significant difference was noted between male and female mice. No remarkable difference was noted between the acute toxicity of the present active substance and those of various known medicaments and antibiotics.

(11) Heat-stability:

The biological activity of the present substance is stable at 100° C. for more than one hour.

In the above-mentioned experiments, the final product obtained by the method of Example 1 described hereinafter was used as test sample of the active substance of the present invention.

The chemical structure of the active substance of this invention has not yet completely been clarified. However, with respect to the above-mentioned physico-chemical and biological characteristics, it is clear that the present active substance is a new substance and is believed to be a kind of high molecular weight glycolipid having an active moiety containing sugar. This substance is different from, for example, the known mitogenic agents such as phytohemagglutinin, pokeweed mitogen and concanavalin A with respect to the fact that these mitogenic agents are proteinic substances having a molecular weight of more than 100,000 and that their interferon-inducing activites are weak and inactivated by heating at 50°–60° C., while the biological activity of the present active substance is not inactivated by heating at 100° C. for more than one hour and its interferon inducing activity is very high.

Also, the characteristics of the present active substance are different from the characteristics of various biologically active substances disclosed by the present inventors. For example, the active substance isolated by us from the seed of pearl barley (*Coix lacryma-Jobi*) exhibits a substantially equal IgE-inhibiting activity to that of the pressent active substance, but has different physico-chemical characteristics such as, e.g. a molecular weight of about 10,000 to 300,000. Also the extraction efficiency of the active substance isolated from pearl barley is lower than that of the present substance.

It has been found that the interferon-inducing activity of the active substance of the present invention is equal or suprior to the corresponding activities originating from the plants of *Perilla* and *Carthamus*, which are highest among various interferon inducers of plant origin of the known types, that the IgE inhibiting activity of the present active substance is equal or superior to the correcponding activity of pearl barley, which is highest among the known IgE inhibiting substances of plant origin and that the mitogenic activity of the present active substance is higher than the corresponding activity of the active substance originating from *Angelica acutiloba*, which is highest among various mitogenic agents of plant origin.

The active substance of this invention may be prepared by a process, which comprises extracting said active substance from the tissue of a plant of the genus zea or a variants thereof capable of producing said active substance and recovering said active substance from the extract thereby obtained.

The plants which may be preferred for the purpose of this invention is maize (*Zea mays* Linne) or a variant thereof. Maize is an annual plant originating in South America and its naturally-occuring parent has not yet been found. Numerous variants of maize have been produced by culturing in various countries of the world and admired as foodstuffs and feedstuffs. Example of the variants viz. mutants and hybrids capable of producing the active substance include flint corn (var. indurata Bail.), sweet corn (var. rugosa Bonaf.), dent corn (var. indentata Bail.), pop corn (var. everta Bail.) and the like. All variants may be used for the purpose of this invention, even though the amount of the active substance contained in the plant tissue may vary with diferring the types of the plants.

It is preferred to extract the active substance of this invention from the floss (corn silk) viz. style and stigma of the plant.

It is known that the floss (style and stigma) of maize contain sistosterol, stigmasterol, vitamin K, glucose, galactan and the like. It is also known that the floss of maize has been used as folk drug and orally administered to humans at a daily dose of not more than 8 g as uretic and cholagogue, with reference to "Saishin Wakan Yakuyo Shokubutsu" (Latest Sino-Japanese Herbal Plants) in Japanese version by T. Karoyone and Y. Kimura, pp. 412–423, published by Hirokawa Shoten, Tokyo, 1980. However, the physico-chemical characteristics of various known substances contained in the floss of maize are different from the characteristics of the active substance of this invention and moreover these known substances have no interferon inducing activity. In the known case, the floss of maize is administered to humans solely and orally for a relatively short period of time. However, with respect the results of the above-mentioned experiments, it is apparently difficult to induce an effective concentration of the active substance of this invention in the body of humans, for example, by oral administration of the floss of maize to humans at a daily dose of 10 g continuously over 4 weeks. Thus, it is clear that the known use of the floss of maize to humans does not recognize both the existence and effect of the present active substance.

For better preservation and extraction, it is preferred to use the ripen and dried floss, although it is possible, if desired, to use the fresh material. The drying method is optional (e.g. natural drying or drying in hot air at low temperature). If desired, the material may be washed with water before use.

The extraction may be effected with water at any convenient temperature, for example, from ambient to the boiling point of the extraction mixture for a period of time from 15 minutes to 7 days, which time may be shortened if the extraction temperature is raised. Thus, extraction may be effected, for example, for a period of 30 minutes to 6 hours at 45°–80° C. with stirring. If desired, the extraction may be effected at about 120° C for several ten minutes.

As the active substance of this invention is particularly soluble in water in alkaline conditions (e.g. pH 7–12), it is possible, if desired, to adjust the pH of water before use, for example, with a suitable buffer solution, sodium hydroxide, potassium hydroxide, ammonium hydroxide and the like. In this case, the extraction on may usually be effected, for example, for 1–5 hours at room temperature.

In this manner, it is possible to extract a major portion of the active substance contained in the starting material (in some cases, more than about 90 %). However, the use of an excessively high temperature should be avoided because the quantity of the undesired impurities such as pigments and low molecular weight substances appearing in the extract may threby increase. It is also possible, if desired, to add a suitable antiseptic agent to the extracting water. The extraction may be effected continuously or intermittently, and any convenient ratio of the extracting water to the raw material may be used.

The residue of the plants is removed from the extracted solution in conventional manner, for exmple, by filtration, pressing or centrifugation. After this, the undesired impurities such as pigments and low molecular weight substances are removed from the resultant supernatant in order to allow recovery of the active exemplified as follows:

(A) The supernatant is fractionated by ultrafiltration e.g. using a suitable membrane for retaining substances having a molecular weight of about 300,000 to about 1,000,000. The ultrafiltration may be effected under a suitable pressure (e.g. 0.1 to 5 kg/square cm). The collected active fractions are combined and freeze-dried to obtain brown powders.

(B) The supernatant is concentrated, if desired, in vacuo and is treated with a hydrophilic organic solvent capable of mixing with the supernatant and incapable of dissolving the active substance (e.g. methanol, ethanol, 1- or 2-propanol, n-butanol, acetone etc.) at a concentration of e.g. 40–70 % w/v so as to form a precipitate containing the active substance, followed by freeze-drying to obtain a brown powder.

(C) Instead of organic solvents, it is possible to add to the supernatant an ammonium salt (e.g. ammonium chloride, ammonium sulfate, cetyltrimethylammonium bromide and the like) or an inorganic metallic salt (e.g. zinc chloride and/or copper chloride) at a convenient concentration (e.g 20–50 w/v %) so as to form precipitates which are desalted in conventional manner, followed by freeze-drying to obtain brown powders.

(D) To the supernatant is added a suitable compound such as e.g. trichloroacetic acid (e.g. 2–10 w/v %)to precipitate proteinic substances. The resultant precipitates are treated in a similar manner to that described above to obtain brown powders.

It is possible to recover the major portion of the active substance contained in the starting material (in some cases, more than 90 %). However, the quantity of impurities contained in the crude brown powders is lowest in the case of method (A), and also method (A) may be effected simply and cheaply. Moreover, it has been confirmed that any sifnificant side effect may be avoided even when a large amount of the crude powder obtained by (A) is orally administered to humans and animals and thus the crude powder may be used for oral administration without further purification.

If desired, the crude powder may further be purified, for example, by column chromatography using a suitable agent for gel filtration or an ion exchanger. In the former case, the elution may be effected with water or a suitable buffer solution. In the latter case, the buffer solution may be adjusted to a pH of 7-9. In order to fractionate a substance having a molecular weight of about 300,000 to about 1,000,000 by using a suitable agent for gel filtration, preferred agents for gel filtration are exemplified by Bio-Gel A (Bio- Rad Laboratories Ltd., U.S.A.), Sephacryl S-300 and Sepharose CL-6B (Pharmacia Fine Chemicals AB., Sweden) and various other agarose-type gel flitration agents. In the case of ion exchange treatment, the active substance substantially passes through anion exchanger such as e.g. CM Sepharose (Pharmacia Fine Chemicals AB., Sweden), CM Toyopearl (Toyo Soda K.K., Japan) and the like, while the active substance may be adsorbed with cation exchange resins such as e.g. DEAE Sepharose (Pharmacia Fine Chemicals AB., Sweden), DEAE Bio-Gel (Bio Rad Laboratories Ltd., U.S.A.), DEAE Toyopearl (Toyo Soda K.K, Japan) and the like at a suitable pH (e.g. 7–9), followed by addition of 0.1–1M sodium chloride to the effluent thereby to separate the active material.

For the purpose of administering the active substance of this invention to humans and animals with good results, an immunopharmacological composition is provided, which comprises as active ingrdient the active substance of this invention, in association with a pharmacologically acceptable carrier or excipient.

The composition may be any and all forms adapted to oral, reactal, parenteral, percutaneous, intramucous administration and the like. Thus, for example, the composition may be solid or liquid for oral administration and may take the forms of powders, stryps, capsules, granules, emulsions, suspensions, drops and the like. Such composition comprise carrier or excipient conveniently used in the pharmaceutical art. Thus, for example, suitable tabletting excipients include lactose, potato and soluble starch and magnesium stearate, and for parenteral administration, the carrier may be a sterile water, physiological solution of sodium chloride, armond oil and the like, which may be put in an ampule or may be added to the active substance before use.

The composition may, if desired, further comprises, for example, bonding agents, stabilizing agents, emulsifiers, suspending agents, dispersing agents, lublicants, antiseptic agents, fillers and the like conveniently used in the pharmaceutical art.

For practical purpose, the composition may be formulated, for example, as buccals, lozenges, eye drops, suppositories and the like for intramucous administration, solutions, oils, suspensions and the like for injection agents, inhalants, sprays and the like for inhalational administration, and ointmens, plasters, liniments, baths, sprays and the like for external administration.

Advantageously, the composition may be formulated as dosage unit forms, each unit being adaptable to supply a fixed dose of active ingredient. Suitable dosage unit forms are, for example, tablets, ampules, capsules, suppositories and the like.

The amount of the active substance preferably contained in such dosage unit forms may, for example, be within a range of about 10-100 for oral administration, about 2-5 for subcutaneous admiistation, about 1.5-5 for intramuscular administration, about 2-10 for buccals and lozenges and about 4-5 for suppositories, caculated on the basis of the preferred amount for intravenous administration. For intravenous administration to humans and animals, it is possible to use, for example, about 0.1-10 mg/kg, although the dose may vary, depending upon various factors such as e.g. the type and age of the hosts, the purpose of administration and the like. When the active substnce of this invention was orally and continuously administered to 5 adults at a daily dose of 200 mg for 30 days, no unusual thing was noted and their feeling was very nice and comfortable.

Examples of dosage unit forms are as follows:

(1) Parenteral injection:

Physiological solution of sodium chloride (1.0 ml), sample (10 mg), packed and sealed in a sterilized ampoule (2 ml)

(2) Lozenge:

White sugar (1 g), sample (50 mg)

(3) Suppository:

Polyethylene glycol 400 (0.8 g), liquid polyethylene glycol 1500 (0.2 g), sample (0.2 g)

(4) Syrup:

CMC-Na (0.2 g), simple syrup (20 g), sodium cyclamate 0.1 g , ethylparaffin (0.04 g), sample (0.1 g)

(5) Ointment:

Purified lanolin (5 g), yellow wax (5 g), white vaselin (87 g), sample (3 g)

(6) Liniment:

potassium hydroxide (0.3 g), glycerin (20 ml), ethanol (25 ml), sample (2.5 g), make up water to 100 ml.

Utility of the Invention (1) The active substance may be produced simply and cheaply. The raw material for the preparation of the active substance of this invention is an agricultural waste.

(2) The active substance of the present invention exhibits interferon inducing activity, polyclonal B cell activating activity, mitogenic activity, macrophage activating activity and anti-tumour activity and is capable of inhibiting the formation of IgE antibodies. Moreover, this substance is capable of enhancing the formation of IgG and IgM antibodies required for protecting against infectious diseases. With respect to the biological activity and low cost, the present active substance is expected, in general, to be useful for maintaining and improving overall health of humans and animals.

(3) Particularly, the active substance of this invention is expected to be useful for preventing and inhibiting various allergic diseases such as e.g. asthema, allergic rhintis as well as various diseases caused or aggravated by the socalled immunological insufficiency such as e.g. rheumatism, B-type hepatitis, AIDS and the like. On the contrary, for example, adrenal cortical hormones (ACH) widely used for treating such diseases have the disadvantage that they can give rise to various undesired side effects such as, for example, the inhibition of the formation of immunoglobulin required for protection of infectious diseases.

The following non-limiting examples and experiments illustrate the present invention.

EXAMPLE 1

300 g of dried floss (style and stigma) of flint corn (*Zea mays* var. *indurata*) purchased in common market in Japan was extracted with water (3 1) for one hour at room temperature and further for one hour at 100° C. The supernatant (2.1 1) was separated from the extracted water by filtration. The residue was washed with water (900 ml) and the washing water was combined with the supernatant. The combined solutions (3 1) were centrifuged (7000 r.p.m./30 min.) to obtain a brownish transparent solution with a yield of 4-5 % on the basis of the starting plant tissue. The resultant extract was treated by ultrafiltration using an unltrafilter (UHP-76, Toyo Kagaku Sangyo K.K., Japan) with Diaflo Membrane XM 300-76 (Amicon Corpn., U.S.A.) at a pressure of 2 kg/square cm in a nitrogen atmosphare for fractionating substances having a molecular weight of more than 300,000. To the collected residual solution, was added several fold greater amount of purified water to repeat the unltrafiltration several times. The residual fraction finally obtained was freeze-dried to obtain 4.197 g of brown powders (Fraction I). It was found that the interferon-inducing activity and ability to inhibit the formation of IgE antibodies of Fraction I were at least several times as much as the corresponding titres of Fraction II which passed through the ultrafilter.

Fraction I (200 mg) was dissolved in a 0.1M tris-HCl buffer solution (pH 7.4; 10 ml) and passed through a column (2.6 X 70 cm) packed with DEAE Toyopearl 650 (Toyo Soda Kogyo K.K., Japan) pre-equilibrated with a similar buffer solution. Elution was effected with a similar buffer solution and the effluent was divided into small fractions (each 20 ml). The first peak appeared in fraction Nos. 7-22 were collected and combined. After addition of 0.2M NaCl, the combined fractions were chromatographed in a similar manner to that described above and fraction Nos. 42-52 were collected and combined. The combined fractions were desalted by ultrafiltration using a PM-10 membrane (Amicon Corpn., U.S.A.) capable of fractionating substances having a molecular weight of not more than 10,000, followed by freeze-drying to obtain amorphous brownish powders (Fraction III; 30.8 mg), of which physicochemical characteristics are as hereinbefore described.

EXAMPLE 2

300 g of dried floss (style and stigma) of dent corn (*Zea mays* var. indentata) purchased in common market in Japan was extracted with water (3 l) with stirring. During the extraction at room temperature for 2 hours, the pH of the extraction mixture was adjusted to 11.0 by adding drops of 1N caustic soda. The extraction mixture was left for 2 hours and filtered to separate the supernatant (2.27 l). The residue was washed with water (800 ml). The supernatant was combined with the washing liquid. The combined solutions were adjusted to a pH of 7.0 with addition of 1N hydrochloric acid. Then the solution was centrifuged (7000 r.p.m./30 min.) to obtain a brownish transparent solution. This solution was treated by ultrafiltration in a similar manner to that described in Example 1. Fractions having a molecular weight of more than 300,000 were collected, combined and the combined fractions were freeze-dried to obtain brown podwers (3.18 g). It was noted that, in comparison with the corresponding powders obtained by the method of Example 1, the resultant brown powders obtained by ultrafiltration contained a lower proportion of low molecular weight fractions and a slightly higher toxicity. The powders were chromatographed using DEAE Toyopearl 650 in a similar manner to that described in Example 1, it was noted that there was no significant difference of the physico-chemical characteristics between the final product obtained in Example 1 and that obtained in this example. Yield: 26.4 mg.

EXPERIMENT 1

Determination of interferon induced by interferon inducer and assay of interferon (Reference: Y. Kojima' report in Kitasato Arch., Med., Exp., 43:35, 1970)

(a) Interferon induction in vitro

A rabbit (weight about 1 kg, Japanese White, SPF) was sacrificed by cardic puncture and its spleen, bone marrow and lymph node cells were collected and combined together, from which a cell suspension containing about $10^7$ mixed cells/ml was prepared using an Eagle MEM medium (Nissui Seiyaku K.K., Tokyo) containing 10 % calf serum. This suspension was divided into fractions (each 1 ml). On each occasion, 10, 1.0, 0.1 or 0.01 μg/ml of a final product prepared by the method of Example 1 was added to the fraction and incubated at 25° C. for 24 hours. Then each culture was centrifuged to obtain a supernatant which was then used as a sample to assay the activity of the interferon induced.

(b) Interferon induction in vivo 2 ml of an aqueous solution of the final product of Example 1 (500 ug/ml) was injected into the auricular vein of a rabbit (weight about 2.5 kg; Japanese White; SPF). 1, 2, 4 and 6 hours after this, a 2 ml sample of blood was removed from the rabbit on each occasion and used to prepare the serum used to determine the interferon activity. (c) In both methods of (a) and (b), the activity of the interferon induced was determined in reliance with the reduction ratio of the plaques in the following manner. A monolayer culture of the lined cells of RK-13 of rabbit was put in a dish and added with a predetermined amount of a suitably diluted solution obtained by the methods (a) or (b). Then the culture was incubated at 37° C overnight. Then the culture was added with Vesicular stomatitis virus as the challenge virus and incubated at 37° C. overnight. The interferon activity was determined in reliance with the reduction ratio of plaques. The unit of the interferon activity is expressed by the reciprocal number of the highest dilution of the sample required for reducing the numbers of plaques to 50 %.

EXPERIMENT 2

Definition of interferon inducer

The samples prepared by the above-mentioned methods (a) and (b) are capable of inhibiting the growth of Vesicular stomatitis virus and Vaccinia virus in the lined RK-13 cells of rabbits of the same animal species, but do not inhibit the growth of Vaccinia virus in L cells of mice i.e. of a different animal species, and moreover, their interferon activities are inactivated by treating with 0.08 w/v % trypsin at 37° C for 2 hours. These results indicate that the active substance of this invention represents an interferon inducer.

EXPERIMENT 3

Inhibition of the formation of IgE antibodies:

(a) Formation of IgE antibodies:

An active substance (4.0 mg) prepared by the method of Example 1 was dissolved in a physiological solution of sodium chloride (4.0 ml) and abdominally administered to each test mouse (BALB/s female, 6 weeks after birth, After this, 2,4-dinitrophenyl egg albumin (10 μg; allergen) mixed with alminium hydroxide gel (4 mg) was abdominally injected to each test mouse. The control mice were treated in a similar manner to that described above without administering the active substance. 14 days after this, blood was removed from each mouse of the test group by cardic puncture and mixed together, from which the serum was isolated and diluted with physiological solution of sodium chloride at different dilution ratios (X 10, X 30, X 100 and X 300 respectively) to prepare the test samples.

(b) Assay of IgE activity by the PCA method (the passive cutaneous anaphylaxie method)

Male rats (weight about 180 g; each group consisting of 5 rats) were used for the test. The hairs on the back of each animal were cleanly shaven, and then the sample of the diluted serum (each 1 ml) was administered to the rat at 20 places under the shaven skin of the animal on each occasion. 4 hours after this, allergen solution (each 1 ml) was injected into the vein at the tail of the animal. The allergen solution was prepared by dissolving 10 ml of dinitrophenyl egg albumin in 10 ml of 1 % Evans blue solution. 30 minutes after this, the animal was anesthetised with chloroform and the skin on the back was peeled off. The blue spots formed at the back of the skin by the reaction were visually detected. In the above-mentioned tables, the mark denotes that the formation of IgE antibodies was completely inhibited so that no blue spot was observed, the mark "±" indicates that a blue spot was formed as a ring around the injected place and the marks ".", ".." and "+++" indicate respectively that the blue spots of the diameters of not more than 10 mm, 11-19 mm and more than 20 mm.

EXPERIMENT 4

Assay of polyclonal B cell activating activity (PBA): (a) In vitro method:

The spleen cells of a BALB/c mouse (female, 8 weeks after birth) was suspended in a medium composed of RPM 1640 medium, 10 % fetal calf serum, 2-mercaptoethanol ($5 \times 10^{-5}$M) and 5 mM Hepes medium. The medium was added with 10 µg or 100 µg of the active substance prepared by the method of Example 1 and incubated at 37° C. for 2 days.

(b) In vivo method:

A sample prepared by the method of Example 1 was abdominally administered to a BALB/c mouse (female, 8 weeks after birth). 3 days after this, the animals was killed to collect the spleen cells.

(c) assay or plaque forming cells (PFC):

The numbers of PFC obtained by the methods (a) and (b) were counted by the method of Cunningham A. J and Szenberg, A (Immunology, 14, 599–601, 1980)

EXPERIMENT 5

Assay of mitogenic activity

The spleen cells of C3H/HeJ mouse or nu/nu mouse (female, 6 weeks after birth) were added to a medium composed of RPM 1640 medium, 10 % inactivated fetal calf serum and 25 mM Hepes medium. The medium was added with a predetermined amount of a sample of the active substance prepared by the method of Example 1 and incubated at 37° C. for 48 hours. 4 hours before completion of culturing, $^3$H-thymidine was added to the medium to investigate the incorporation of $^3$H-thymidine. Stimulation index (SI) was calculated with reference to control medium containing no active substance.

EXPERIMENT 6

Assay of ajuvant activity

A sample of the active substance prepared by the method of Example 1 (10 or 100 µg) and about $10^7$ of sheep red cells were abdominally administered to BALB/c mouse (8 weeks after birth, female, each group consisting of 5 mice). 4 days after this, PFC (plaque forming cells) were assayed by the Cunningham and Szenberg method using sheep red cells specific to the target cells and trinitrophenylated horse red cells (TNP-HRBS) non-specific to the target cells.

EXPERIMENT 7

Assay of macrophage activating activity

Macrophages were collected from BALB/c mouse (6 weeks after birth, female, each group consisting of 5 mice) by abdominal injection of thioglycolate and mixed with the active substance (10, 30 or 100 µg) prepared by the method of Example 1. On each occasion, the mixture was combined with the cells of EL-4 leukemia and incubated at 37° C. for 40 hours. 16 hours before completion of culturing, $^3$H-thymidine was added to the culture. The determination was effected after completion of culturing.

EXPERIMENT 8

Assay of IMC ascites tumor

IMC ascites tumor cells (about $10^6$ cells) were administered to CDF$_1$ mice (6 weeks after birth, female, each group consisitng of 5 mice) by abdominal injection. After this, the active substance prepared by the method of Example 1 dissolved in physiological solution of sodium chloride was abdominally adminstered to the test mice at a daily dose of 25, 5 or 1 mg/kg over a period of 2 weeks beginning the next day after administration of the tumour cells.

EXPERIMENT 9

Assay of Ehrlih ascites tumor

Mice (ddY, 6 weeks after birth, female, each group consisting of 5 mice) were treated in a similar manner to that described in Experiment 8 except the use of $2 \times 10^5$ Ehrlich ascites tumor cells instead of IMC ascites tumor cells.

EXPERIMENT 10

BALB/c female mice (6 weeks after brith, body weight about 20 g) were divided in to 6 groups, each consisting of 6 mice. The active substance prepared by the method of Example 1 was dissolved in a small amount of water and abdominally administered to the test animals in amounnt of 5 µg No. 2), 25 µg (No. 3), 100 µg (No. 4) and 400 µg respectively. Then as allergen 2,4-dinotrophenol (each 10 mg) dissolved in 0.2 ml of physiological solution of sodium chloride was abdominally administered to each of the test animals. The control animals were administered with the allergen alone. 14 days after this, blood was collected from the venous plexus in the eype pit of all animals and mixed together, from which the serum was collected and used to assay the IgE-antibody titre by the passive cutaneous anaphylaxie (PCA) method disclosed in item (b) of Experiment No. 3 as hereinbefore described by using rats as test animals, each of which was injected by the allergen (10 mg) dissolved in 10 ml of 1 % Evans solution (10 ml).

The results are shown in the following table. In this table, A and B denote respectively the amount of the active substance (mg/kg; adminstered by i.p.) and the IgE antibody titre expressed by the dilution ratio. Where the active substance was injected (i.p.) to the animals in an amount of 400µg/Kg, 5 of 6 animals were killed one or two days after the injection owing to the acute toxicity of the active substance so that the antibody titre was unmeasurable. The tests were repeated 4 times.

TABLE 14

|  | IgE-antibody titre | | | |
|---|---|---|---|---|
|  | 1 | 2 | 3 | 4 |
| Control | 128 | 128 | 64 | 128 |
| 5 µg | <16 | 16 | 16 | 16 |
| 25 | <16 | <16 | <16 | <16 |
| 25 | <16 | <16 | <16 | <16 |
| 100 | <16 | <16 | <16 | <16 |

We claim:

1. A water-soluble, biologically active substance isolated from a tissue of a plant selected from the plants of the genus Zea and variants thereof capable of producing said active substance, said active substance being capable of inhibiting the formation of IgE antibodies and promoting the formation of IgG and IgM antibodies and having interferon inducing activity, polyclonal B lymphocite activating activity, mitogenic activity, adjuvant activity and anti-tumour activivty, and when substantially purified being in the form of light brownish powder having the following physico-chemical characteristics:

(1) Elementary analysis:
 H: 5.20–5.40 %, C: 42.55–44.17 %, N: 3.94–4.08 % (Ash: 0.057 mg in 1.834 mg of sample)
(2) Molecular weight:
 About 300,000—1,000,000 by gel filtration
(3) Melting point or decomposing point:
 Melting point is indefinite Decomposed at about 220° C.,
(4) Ultraviolet absorption spectrum:
 As shown in FIG. 1 (0.1N NaoH)
(5) Infrared absorption spectrum:
 As shown in FIG. 2 (KBr method)
(6) Solubility in various solvents:
 Soluble in water, readily soluble in aqueous solutions of potassium hydroxide, sodium hydroxide, ammonium hydroxide, potassium carbonate etc. and hardly soluble in methanol, ethanol, propanol, butanol, acetone, chloroform and ether
(7) Color reaction:
 Positive in ninhydrin reaction, phenol/sulfuric acid reaction and Dittmer's reaction Negative in Morgan/Elson's reaction
(8) Nature: acidic substance
(9) Main chemical constituents:
 (A) Amino acid:

| | |
|---|---|
| aspartic acid 1.96±0.02, | threonine 1.17±0.02, |
| serine 1.16±0.05, | glutamic acid 1.42±0.01, |
| proline 0.94±0.01, | glycine 2.07±0.03, |
| alanine 1.71±0.03, | cystine 0.12±0.01, |
| valine 1.00±0.03, | methionine 0.09±0.02, |
| isoleucine 0.51±0.01, | leucine 1.00, |
| tyrosine 0.35±0.05, | phenyalanine 0.60±0.01, |
| lysine 0.55±0.02, | histidine 0.18±0.01, |
| arginine 0.48±0.02, | ammonia 4.27±0.22, | expressed by the ratio of concentration on the basis of 55.11n mol of leucine
 (B) Sugars: (molar ratio, %), rhamnose (5.9), arabinose (3.8), xylose (4.4), mannitol (1.0), galactose (1.8), glucose (18.9), hexose in total (50.6) by phenol/sulfuric acid method, uronic acid in total (10.5 %) by metahydroxy/diphenyl method
(10) specific rotation: $[\alpha]_D^{25} = +30\text{--}36°$ (33° in average), c = 1 mg/ml water.

2. A process for producing the water-soluble, biologically active substance, of claim 1 from a plant tissue, said biologically active substance being capable of inhibiting the formation of IgE antibodies and promoting the formation of IgG and IgM antibodies and having interferon-inducing activity, polyclonal B lymphocite activating activity, mitogenic activity, adjuvant activity and anti-tumour activity, which comprises, the steps of extracting said active substance with water from the tissue of a plant selected from the plants of the genus Zea and variants thereof capable of producing said active substance at a temperature of from ambient to the boiling point of the extraction mixture for a period up of 15 minutes to 7 days sufficient to extract the major portion of said active substance present in said plant tissue, forming a supernatant from the extracted solution, fractionating the supernatant to yield fractions containing the major portion of said active substance present in the supernatant, and recovering said active substance therefrom.

3. The process of claim 2, wherein said plant is selected from the plants of *Zea mays* Linne and variants thereof.

4. The process of claim 2, wherein the plant tissue is the floss.

5. The process of claim 2, wherein the extraction is effected under alkaline conditions.

6. The process of claim 5, wherein the extraction is effected at a pH of from 7 to 12.

7. The process of claim 2, wherein the supernatant is fractionated by ultrafiltration.

8. The process of claim wherein the ultrafiltration is effected by using a membrane capable of retaining substances having a molecular weight of more than 300,000.

9. The process of claim 2, wherein the supernatant is fractionated by adding to the supernatant one member selected from hydrophlic organic solvents capable of mixing with the supernatant and incapable of dissolving said active substance, ammonium salts and trichloroacetic acid so as to form a precipitate containing the major portion of said active substance present in the supernatant.

10. A pharmaceutical composition, comprising as active ingredient, a biologically active substance as claimed in claim 1, in association with a pharmaceutically acceptable carrier or excipient.

* * * * *